US012594358B2

(12) United States Patent
Aner, Sr.

(10) Patent No.: US 12,594,358 B2
(45) Date of Patent: Apr. 7, 2026

(54) NATURAL METHOD OF REDUCTION AND REMOVAL OF PATHOGENIC AGENTS AND MICROORGANISMS CONTAINED IN SOLIDS

(71) Applicant: Andres Adalberto Aner, Sr., Buenos Aires (AR)

(72) Inventor: Andres Adalberto Aner, Sr., Buenos Aires (AR)

( * ) Notice: Subject to any disclaimer, the term of this patent is extended or adjusted under 35 U.S.C. 154(b) by 418 days.

(21) Appl. No.: 16/720,911

(22) Filed: Dec. 19, 2019

(65) Prior Publication Data

US 2020/0121823 A1     Apr. 23, 2020

Related U.S. Application Data

(62) Division of application No. 15/480,943, filed on Apr. 6, 2017, now Pat. No. 10,765,772.

(51) Int. Cl.
| | |
|---|---|
| *A61L 2/00* | (2006.01) |
| *A61L 11/00* | (2006.01) |
| *B02B 1/08* | (2006.01) |
| *B02C 17/00* | (2006.01) |
| *B02C 18/06* | (2006.01) |
| *B02C 18/22* | (2006.01) |
| *B09B 3/40* | (2022.01) |
| *A61L 2/04* | (2006.01) |
| *B02C 18/14* | (2006.01) |

(52) U.S. Cl.
CPC .............. *A61L 11/00* (2013.01); *B02C 18/06* (2013.01); *B02C 18/2233* (2013.01); *B09B 3/40* (2022.01); *A61L 2/04* (2013.01); *B02C 18/146* (2013.01); *B02C 2201/06* (2013.01)

(58) Field of Classification Search
CPC ..... A61L 2/00; A61L 2/04; A61L 2/07; A61L 11/00; B09B 3/0083; B02C 18/2233; C07C 45/59; C07C 45/60; C07C 37/54; C07C 49/395; C07C 49/597
USPC ........ 422/1, 26–28, 32–33, 184.1, 261, 292, 422/295, 297, 300, 307–309; 34/523; 241/65, 171, 185.5, 606
See application file for complete search history.

(56) References Cited

U.S. PATENT DOCUMENTS

| | | | | |
|---|---|---|---|---|
| 5,167,372 A * | 12/1992 | Poggie | ...................... | A61L 2/06 |
| | | | | 241/23 |
| 5,656,248 A * | 8/1997 | Kline | ...................... | A61L 11/00 |
| | | | | 422/295 |
| 8,562,916 B2 * | 10/2013 | Yamanobe | .............. | A61L 11/00 |
| | | | | 241/606 |

(Continued)

*Primary Examiner* — Monzer R Chorbaji

(57) ABSTRACT

A machine to carry out the method for the reduction or removal of pathogenic agents and microorganisms contained in solids, comprising a front chamber for the entrance of the material; a contiguous rear chamber associated with the entrance chamber, by means of which the processed material is expelled; said contiguous rear chamber containing a grinding means that rotates when it is actuated by an engine; and a piston that enters into the front chamber running along said chamber into the rear chamber until it reaches a grinding means, where the grinding means consists of a solid, hard and heavy cylinder associated with a transverse axis, said cylinder being provided with a set of longitudinal slots from base to base that form edges with the cylinder surface and where the space between the cylinder surface and the rear chamber inner wall is smaller than 5 mm.

8 Claims, 4 Drawing Sheets

(56)                    References Cited

U.S. PATENT DOCUMENTS

2010/0145005  A1 *   6/2010   Hitzler ............... B29B 17/0026
                                            528/502 C

* cited by examiner

NATURAL METHOD OF REDUCTION AND REMOVAL OF PATHOGENIC AGENTS AND MICROORGANISMS CONTAINED IN SOLIDS

CROSS-REFERENCE TO RELATED APPLICATIONS

The present application is a division of my application Ser. No. 15/480,943 filed on Apr. 6, 2017, entitled NATURAL METHOD OF REDUCTION AND REMOVAL OF PATHOGENIC AGENTS AND MICROORGANISMS CONTAINED IN SOLIDS, which claims Paris Convention Priority date of Aug. 16, 2016, based on Argentine patent application number (AR) 20160102511.

This invention is directed to a method and a machine for the reduction and/or removal of pathogenic agents and microorganisms in solids by means of physical mechanisms. The method may be used for the treatment of urban wastes or organic wastes from factories that produce organic wastes or for the reduction and/or removal of pathogenic agents and microorganisms of food which process requires the grinding of raw material and, in general, for the grinding and reduction and/or removal of pathogenic agents and microorganisms in solids.

BACKGROUND

The treatment of solids having organic contents, the disposal of waste and, particularly, the disposal of waste masses are a current problem, with public dumping sites being rapidly filled up and contaminating leachates therefrom being a frequent contaminant of waterways. Urban and industrial wastes always contain or degrade forming toxic products or polluting gas products.

The processes frequently used for the treatment of this kind of wastes containing organic products are usually thermal, biological or chemical processes. The problems associated with said current thermal treatments include the need of making high investments and high maintenance costs mainly due to the energy cost and physical conditions that make it difficult to apply them. As far as biological and chemical treatments are concerned, there also arise problems related to the required high investments as well as a high consumption of reactants, and, consequently, associated high costs of exploitation, a high production of treatment process wastes and the existence of physical constraints that also make it difficult to apply them.

Likewise, said wastes are usually treated and disposed of by means of cementation and burial or dumping of the solid waste product. This method of disposal has the problem of disposal of the supernatant liquid of the cementation process as well as the disposal of an increased volume of solid material which may often leach.

For example, patent WO 90/12251 discloses a method and an apparatus for waste treatment that includes grinding bulk wastes from a broad variety of sources, mixing the waste material with a binder, granulating the mixture, coating the granules with a refractory material and subjecting the mixture to combustion within a furnace at a temperature above 1300 degrees Celsius (2372.00° F.).

Likewise, patent WO 9701064 A1 discloses a method of mud treatment to achieve a non-explosive mixture that may be incinerated.

It seems difficult to omit the incineration process, which, although on the one hand neutralizes toxic organic elements, the result thereof pollutes the environment.

At present, for the disposal of said wastes, besides the incineration system, the Controlled Dump system is used. The Controlled Dump is the most commonly used means and one of its main problems is its relative short life due to a rapid saturation. On the other hand, the current guidelines of the European Economic Community with regard to this kind of dumps require that the risk of wastewater pollution by leachates be eliminated and that a suitable treatment be provided to the biogas that may be produced, all of which is costly and difficult to comply with in practice. The trend in the treatment of waste having organic contents is the biological treatment for obtaining biogas. The energy contained in the vapor that is released from the remaining mud is also usually leveraged and, finally, said mud is dried and incinerated.

DESCRIPTION OF THE INVENTION

This invention is directed to a natural method of reduction and/or removal of pathogenic agents and microorganisms in solids by means of a physical-thermal mechanism.

The proposed method consists in grinding and heating—without incineration—solid materials from different sources.

The solid materials that are the subject-matter of this method:

do not require a previous grinding, except the extraction of extremely hard materials which volume exceeds 100 cm³ (6.10 inch³), such as paving stones, boulder, metals, etc.

are previously adjusted to a preferred humidity degree by means of the addition of water or aggregates (rubble, bricks, clay, ash) in order to increase or decrease their humidity, respectively.

The device used for the execution of the method comprises a material feeding trough (1) connected to a front chamber (2) by means of a gate (3); said front chamber (2) drives an hydraulic piston (4) that pushes the material towards a rear chamber (5) containing a quasi-solid cylinder (6), a gate (7) that separates both chambers according to the device version, and another gate (8) that is actuated by means of another hydraulic piston (9) that enables the discharge of the already processed material. Likewise, the machine has means to rotate the cylinder (6) and pressure and temperature control and regulation means linked to the controls of the piston (4) and the engine associated with the cylinder (6).

The solids so prepared enter through the feeding trough (1) into the front chamber (2), after which there is another rear chamber (5) that contains on its rear end a quasi-solid cylinder (6) that rotates around a longitudinal axis (10) that transversely passes through the rear chamber (5). Said cylinder (6) includes on its surface longitudinal slots (11) having sharp edges (12) of between 60 and 120 degrees, preferably between 80 and 100 degrees. These longitudinal slots (11) play the role of bump, dragging, crushing, grinding, and friction of the entered solid material. The rear chamber (5) containing the cylinder includes an exit gate (8) in its rear end in order to enable the exit of the processed material.

The front chamber (2) includes on its upper end an opening for the entrance of a piston (4) having a concave surface in correspondence with the surface of the quasi-solid cylinder (6).

The rear chamber consists of two sections, a front section in correspondence with the front chamber in order to enable the piston passage between both chambers and a rear section that contains the cylinder and which wall, in correspondence with the cylinder shape, is concave, as a drum section, thus forming a cylindrical surface, with a tiny light (14) between said walls and the cylinder for the movement of the material under process. Said light (14) has a distance of up to 5 mm (0.19685 inch), preferably between 1 mm (0.0393701 inch) and 5 mm (0.19685 inch) and said light (14) is uniform along the whole concave section of said wall.

The device used to carry out the process has two versions, one of which is in upright position (FIG. 1) and the other one is in a horizontal position (FIG. 2).

In the case of the device in a horizontal position (FIG. 2), between the entrance trough (1) and the base of the front chamber (2) there is an intermediate cap or gate (3) associated with the piston that prevents wastes from entering when the piston (4) moves towards the rear chamber (5). The cylinder (6) starts rotating at high speeds and the piston (4) moves into the front chamber (2) closing the trough (1) and pushing the material towards the cylinder (6).

The cylinder (6), by means of its longitudinal slots (11), while rotating, bumps, crushes and grinds the solid material and at the same time it centrifugally expels said material towards the piston (4). The piston (4) moves forward towards the cylinder (6) until finally the resulting product as a dough increases its temperature mainly owing to the pressure increase caused by the piston, the centrifugal force of the cylinder, and the friction caused by the cylinder (6) against the dough. At a certain pressure and when a part of the dough becomes powdered, the dough moves between the cylinder surface (6) and the light that remains between the cylinder and the concave wall (13) of the rear chamber (5), being subjected to a greater friction and converted into a ground and homogeneous dough, thus making the rapid and homogeneous distribution of heat in the material easier. The water vapor produced by the process, acting at a high pressure, is not only responsible for most of the temperature increase and the homogeneous distribution of heat in the mixture but also it acts as a pressure retainer mixed with the dough.

Once the desired temperature and exposure times have been reached, the exit gate (8) opens and the inner pressure is released thus leveling both (inner and outer) pressures. The first element that exits is water vapor and the second one is the processed dough.

The joint action of the temperature and vapor causes the coagulation of the microorganism proteins, among which there are essential proteins for the microorganism life and reproduction, consequently, this fact leads to their destruction.

The grinding of the wet material until it becomes a dough eases the action of temperature and vapor, thus ensuring that said physical-chemical conditions reach all of the material.

In the upright position device version (FIG. 1), the material enters into the trough (1) and falls onto a gate (7) that separates the front chamber (2) from the rear chamber (5). When the material load is finished, the gate (3) of the trough (1) is closed, the cylinder (6) starts rotating at high speeds, the gate (7) that separates both chambers (2 and 5) opens and the piston (4) moves forward into the tunnel formed by the front chamber (2) and the rear chamber (5) thus pressing the material against the cylinder (6).

PREFERRED EMBODIMENTS

Figure 1:
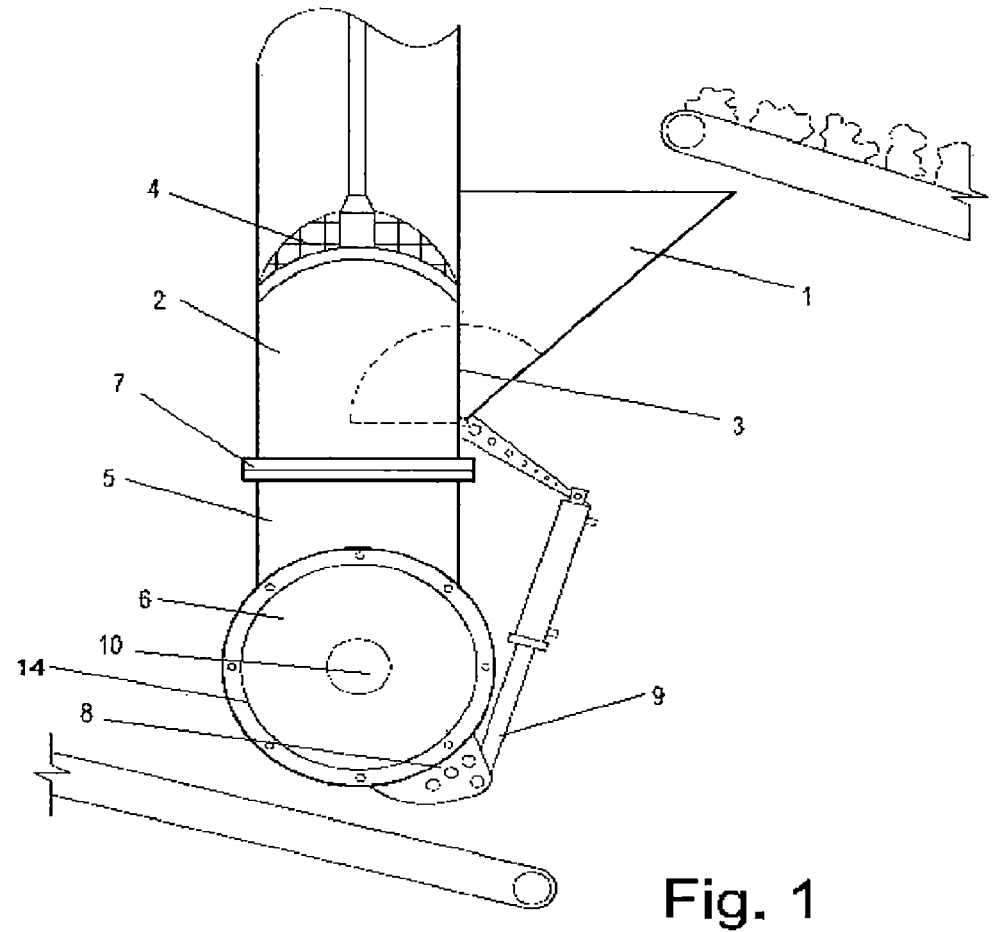
FIG. 1 represents the device in upright position.
Figure 2:
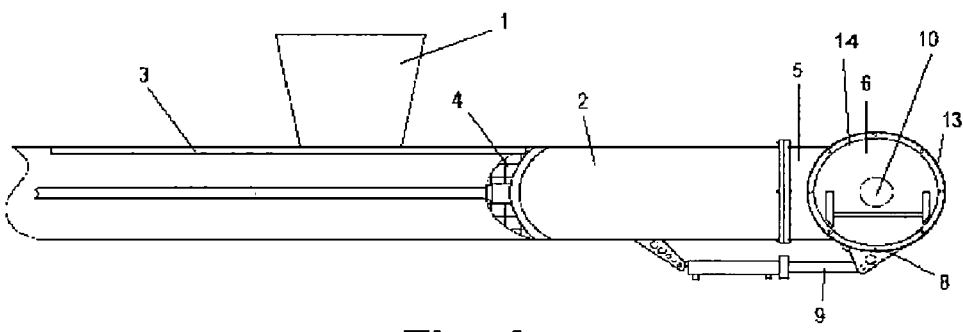
FIG. 2 represents the device in a horizontal position.

As there arises from the description of the invention, the method consists of the following steps:
Purification of the starting material
Adjustment of its humidity degree
Load of the material
Simultaneous grinding and heating of the material at high pressure
Discharge of the obtained dough
a) Purification of the Starting Material
The starting materials of this method do not have uniform contents, sizes, or hardness and must be previously purified in order to preserve the grinding mechanism. The grinding mechanism might be damaged by the presence of materials that combine a big size and an extreme hardness and malleability. For example, metals are extracted in view of their difficulty being ground, paving stones and boulder exceeding a volume of about 100 cm³ (6.1023744094732 inch³) whenever they do not enable an easy grinding or compromise the integrity of the machine because of their size and hardness. For example, if the starting material is fragile, such as animal bones and fat as waste of the food industry, a starting purification shall not be necessary in view of the fragility of the bone, which shall be broken by the piston action.
b) Adjustment of the Humidity Degree
In order to carry out the method and achieve the simultaneous grinding and heating, humidity plays a significant role to optimize said process. In this sense, in this step, aggregates, ash, and/or rubble will be added or a previous drying process will be used in order to reduce the percentage humidity of the starting material, otherwise water should be added.
c) Material Load
The material is loaded through the trough (1) into the front chamber (2).
d) Simultaneous Grinding and Heating of the Material at High Pressure
The material enters into the machine through the trough (1) towards the front chamber (2) that receives the material. The cylinder (6) starts rotating up to the process starting speed. Once the entrance of the material has been completed, the gate (3) of the trough (1) is closed and the piston (4) moves onto the material.
The material contacts the cylinder (6) that is rotating at high speed and the edges (12) of the slots (11) of the cylinder attack the material. Simultaneously, the piston (4) exerts pressure onto the material towards the cylinder (6). The cylinder (6) speed and the shape of its slots (11), by the action of the centrifugal force, prevent the material from entering into the slots (11) of the cylinder (6). Likewise, the edges (12) of the slots grind the material until it becomes powdered.
When the material becomes a dough, said dough is dragged by the cylinder (6) between the light (14) existing between said solid and the inner cylindrical surface (13) of the rear chamber (5) thus contributing to
further reduce the size of the material particles. Owing
to both friction and the pressure increase, heat is
created, which increases the dough temperature and, in
turn, the existence of vapor at high pressure and the
reduction of the material particle size 1 contribute to a
more rapid and uniform heat distribution.

Once the target temperature has been obtained, it is kept
during the target time in order to achieve the reduction
and/or removal of the pathogenic material and micro-
organisms.

e) Discharge of the Obtained Dough

Once the process has finished, the inner and outer pres-
sures are balanced, the discharge gate (8) is opened and
the material is expelled.

Thus, for example, the process may be carried out at a
target temperature from 72 to 91 degrees Celsius (from
161.6 to 195.8° F.) for 3 to 15 seconds or from 92 to 138
degrees (197.6 to 280.4° F.) for 5 to 20 seconds, or other
values that are part of the state of the art with regard to the
removal of pathogenic material and reduction of the amount
of microorganisms.

In order to achieve a greater reduction of the pathogenic
material and microorganisms in the material, it is possible to
use a target temperature from 115 to 136 degrees Celsius
(239 to 276.8° F.) for 21 seconds to 3 minutes or other values
of a process of reduction and/or removal of pathogenic
agents and microorganisms that are part of the state of the art
and generally associated with pasteurization and steriliza-
tion processes.

Likewise, humidity may be added also in the humidity
adjustment step by means of an acidic solution in order to
vary the pH of the medium and contribute to the efficiency
of the process of pathogenic material removal and reduction
of the amount of microorganisms.

The operating pressure of the machine may reach 7
kg/cm², preferably a pressure from 2 to 5 kg/cm² to carry out
the process and the operating speeds of the cylinder (6) are
between 2400 and 4000 rpm (revolutions per minute), which
will enable to reach the proposed temperatures.

Both the piston (4) pressure and the cylinder (6) speed are
subject to the target temperature. Therefore, pressure and
speed are determined by the target temperature of the
process. The machine includes temperature sensors associ-
ated with the engine that actuates the cylinder (6) and the
piston (4) in order to regulate the cylinder (6) speed and the
piston (4) pressure so that the target temperature is achieved
and kept during the desired time.

The quasi-solid cylinder (6) is given this name because it
includes a series of slots or cuts (11) along the cylinder
trunk, from base to base and from the surface and towards
its inner axis, which preferred depth is of at least a tenth part
of the cylinder diameter, thus forming rims or edges (12) on
the cylinder trunk surface, which attack the material and
grind it. Said slots (11) are spaced along the diameter in an
enough amount and with an enough size so as not to weaken
the cylinder structure (6) for the work it must do. In the
accompanying figures, the cylinder includes six evenly
distributed slots.

Figures 3, 4:
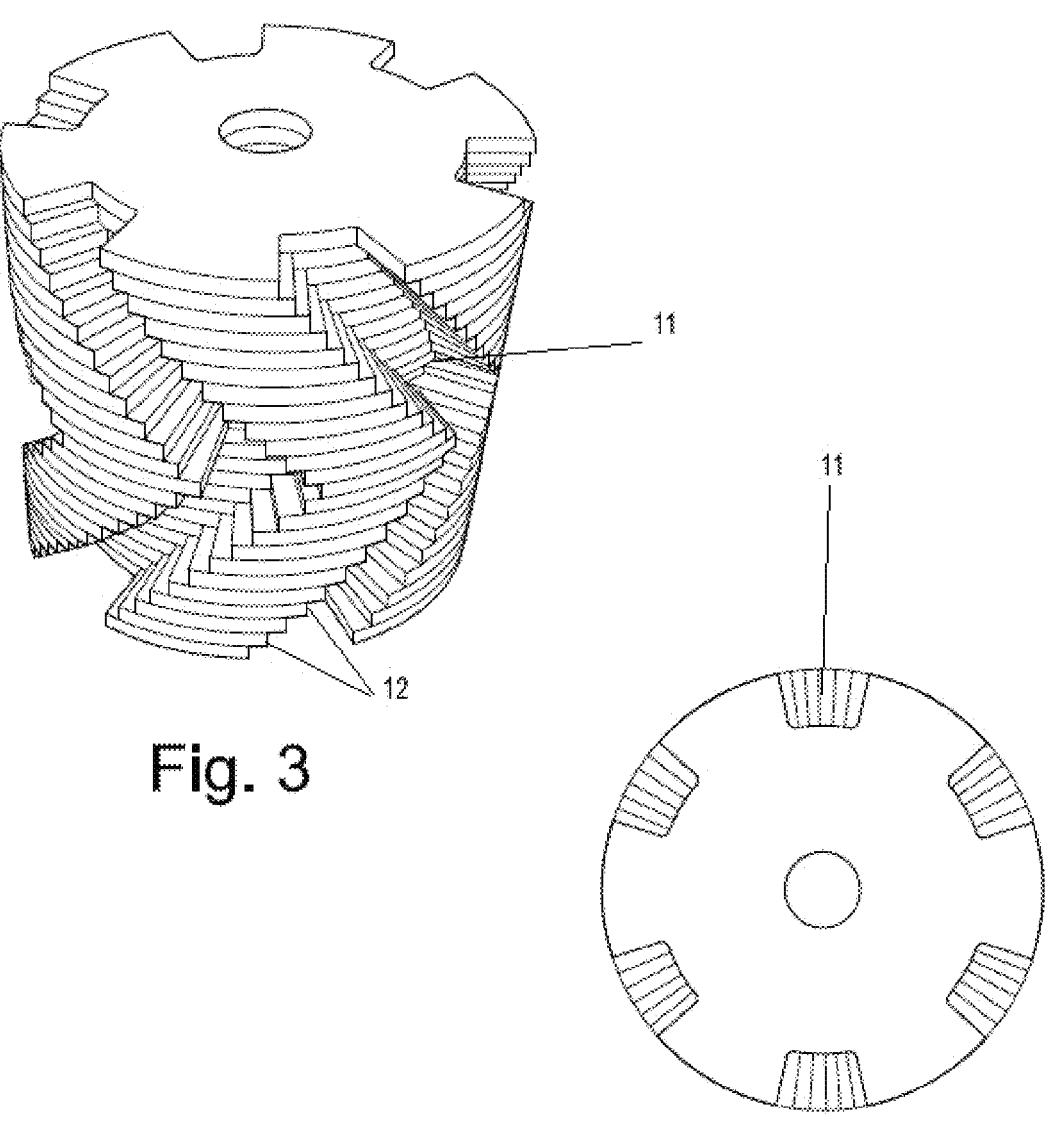
FIG. 3 is a side view of the quasi-solid cylinder with longitudinal slots with a vertex.
FIG. 4 is a top view of the quasi-solid cylinder with longitudinal slots with a vertex.
Figure 5:
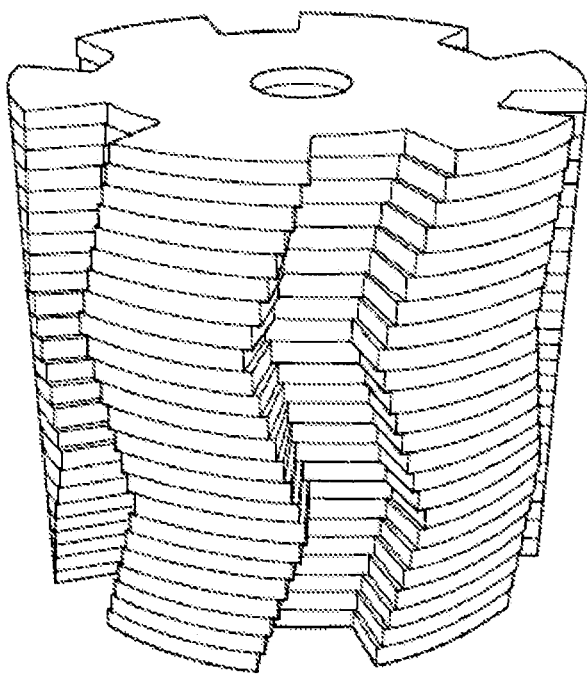
FIG. 5 is a side view of the quasi-solid cylinder with longitudinal slots with two vertexes.
Figure 6:
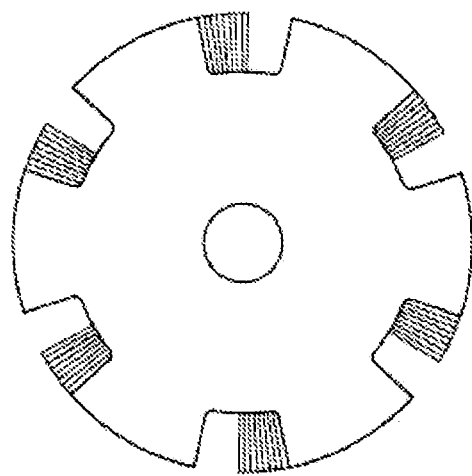
FIG. 6 is a top view of the quasi-solid cylinder with longitudinal slots with two vertexes.

Said slots are V shaped in a cylinder version (FIGS. 3 and
4) formed by a vertex. In another version of the cylinder, the
slots have a bigger angle between the sides that form the
vertex and have two vertexes (FIGS. 5 and 6).

The slots and edges thereby formed may also be teethed,
as shown in the accompanying figures. Said feature contrib-
utes to the grinding efficacy since it creates a significant
amount of vertexes on the edge thus increasing the grinding capability. Said feature also results from the practicality and
economy that derive from the cylinder assembly as a series
of cylindrical plates with a shape corresponding to the
cylinder base that stack up and successively move to form
the slots and then said cylindrical plates join together to form
the cylinder (6).

Furthermore, the angle formed by the slots with regard to
the trunk surface is relevant. Said angle, as may be seen in
the top view of the cylinders is slightly above 90 degrees.
Said aspect is convenient so that a centrifugal force is
created with regard to the area within the slot when the
cylinder rotates. At the same time, it is not convenient that
said angle be much greater than 90% in view of the fact that
the efficacy in the action of the edges would be lost when the
material is ground.

The cylinder must be build with material of a hardness
and weight that enables the grinding of any kind of material,
in a rapid and effective way, without compromising the
integrity of the machine. In this sense, the cylinder will be
perfectly balanced on a hard, rigid and perfectly straight
axis, which will enable the stable and safe rotation at great
speeds.

The so formed quasi-solid cylinder with the drum con-
taining it and the small light (14) between them is respon-
sible for the thorough grinding of the material and, conse-
quently, it has been formed with slots in a solid body since
if it were formed with protruding parts and without the
safeguard of a solid body to bear the stress, it would cause
a rapid wear of the protruding parts as well as an eventual
breakdown and detachment of said protruding part with the
risk it represents for the integrity of the machine and its
operators.

EMBODIMENT EXAMPLE

For a concrete case of material treatment, 10 kgs of solid
material are added, said solid material being composed of
organic and inorganic waste with 23% humidity content.
The piston (4) moves towards the cylinder but without
exerting pressure onto the dough. The material collides with
the cylinder that is rotating at a speed of 2400 rpm, thus
starting breaking and grinding the material. Next, the piston
moves onto the material increasing the pressure up to 5
kg/cm2 and at the same time the cylinder increases its
rotation speed to reach a speed of 3800 rpm. In this way, the
material is powdered and there is a significant pressure
increase that alters the composition of said dough as well as
a temperature increase until the target temperature is reached
which turns out to be uniform in all of the particles of said
dough. Once the temperature is reached, the process ends
with the opening of the discharge gate from which unpol-
luted water vapor and the material processed as an inert,
unpolluted dough, free of pathogenic agents and microor-
ganisms exit.

The invention claimed is:

1. A machine to carry out the method of reduction and
removal of pathogenic agents and microorganisms con-
tained in solids, comprising: a front chamber for the entrance
of the material to be processed; a contiguous rear chamber
associated with the front chamber, by means of which the
processed material is expelled; said contiguous rear chamber
containing a grinding means that rotates when it is actuated
by an engine; and a piston that enters into the front chamber
running along said front chamber into the rear chamber until
it reaches the grinding means, wherein the grinding means
consists of a solid cylinder associated with a transverse axis,
said solid cylinder being provided with a set of continuous longitudinal slots from the upper base to the lower base of the solid cylinder that form edges with the solid cylinder surface and the rear chamber that contains the solid cylinder has an inner concave wall, in correspondence with the solid cylinder shape, forming a cylindrical surface, with a space between the cylindrical surface and the solid cylinder that is not greater than 5 mm.

2. The machine of claim 1, wherein the shapes of the longitudinal slots are selected from the following options:

U-shaped profile;

V-shaped profile;

U-shaped profile and with a longitudinal shape with a vertex (elongated V shape);

U-shaped profile and with a longitudinal shape with more than one vertex;

V-shaped profile and with a longitudinal shape with a vertex (elongated V shape);

V-shaped profile and with a longitudinal shape with more than a vertex.

3. The machine of claim 2, wherein the solid cylinder includes on its surface longitudinal slots having sharp edges that form an angle with the solid cylinder that is greater than 90%.

4. The machine of claim 3, wherein the solid cylinder includes on its surface longitudinal slots having sharp edges that form an angle with the solid cylinder that is greater than 90° and smaller than 100°.

5. The machine of claim 1, wherein the longitudinal slots are evenly distributed around the cylindrical surface.

6. The machine of claim 5, wherein the number of the longitudinal slots is between 6 and 8.

7. The machine of claim 1, wherein the edges formed with the solid cylinder surface are teethed.

8. The machine of claim 1, wherein the space existing between the solid cylinder and the cylindrical surface of the rear chamber containing the cylinder is smaller than 5 mm.

\* \* \* \* \*